(12) United States Patent
Piovanelli et al.

(10) Patent No.: US 9,613,436 B1
(45) Date of Patent: Apr. 4, 2017

(54) OPTIMIZATION METHODS FOR FEATURE DETECTION

(71) Applicant: Sensing Electromagnetic Plus Corp., Palo Alto, CA (US)

(72) Inventors: Matteo Piovanelli, Palo Alto, CA (US); Alessandro Levi, Palo Alto, CA (US); Silvano Furlan, Palo Alto, CA (US)

(73) Assignee: Sensing Electromagnetic Plus Corp., Palo Alto, CA (US)

( * ) Notice: Subject to any disclaimer, the term of this patent is extended or adjusted under 35 U.S.C. 154(b) by 164 days.

(21) Appl. No.: 14/580,173

(22) Filed: Dec. 22, 2014

Related U.S. Application Data

(60) Provisional application No. 61/920,432, filed on Dec. 23, 2013.

(51) Int. Cl.
  *G06T 11/00* (2006.01)
  *G01N 23/04* (2006.01)

(52) U.S. Cl.
  CPC .......... *G06T 11/003* (2013.01); *G01N 23/046* (2013.01)

(58) Field of Classification Search
  CPC ... G06T 7/0042; G06T 11/003; G06T 11/005; G06T 2207/10072; G06T 2207/10081; G06K 9/00496; G06K 9/00523; G06K 9/46; G01N 23/046; A61B 6/032; A61B 6/5205
  See application file for complete search history.

(56) References Cited

U.S. PATENT DOCUMENTS

| | | | |
|---|---|---|---|
| 7,650,331 B1 | 1/2010 | Dean et al. ....................... 707/3 |
| 2004/0136501 A1* | 7/2004 | Boyd et al. ................... 378/210 |
| 2013/0108007 A1 | 5/2013 | Yin et al. .......................... 378/4 |
| 2014/0133707 A1* | 5/2014 | Park et al. ............ G06T 7/2033 382/107 |

FOREIGN PATENT DOCUMENTS

WO   2012050510 A1   4/2012

* cited by examiner

*Primary Examiner* — Andrew W Johns
(74) *Attorney, Agent, or Firm* — Cooley LLP

(57) ABSTRACT

An apparatus includes a processor and a memory connected to the processor. The memory stores instructions executed by the processor to perform a transformation on a detected signal that has penetrated an object of interest to form a sinogram. The sinogram is a sine-based representation of the detected signal. A feature of interest is identified in the sinogram. A tomogram corresponding to the detected signal is reconstructed. The instructions to reconstruct utilize the feature of interest to determine at least one attribute of the tomogram.

9 Claims, 12 Drawing Sheets

OPTIMIZATION METHODS FOR FEATURE DETECTION

CROSS-REFERENCE TO RELATED APPLICATION

This application claims priority to U.S. Provisional Patent Application Ser. No. 61/920,432, filed Dec. 23, 2013, the contents of which are incorporated herein by reference.

FIELD OF THE INVENTION

This invention relates generally to signal processing. More particularly, this invention relates to optimized methods for feature detection.

BACKGROUND OF THE INVENTION

Tomography refers to imaging by sectioning or sections using any kind of penetrating signal or wave. A device used in tomography is called a tomograph, while the image produced is a tomogram. In most cases tomography is based upon the mathematical procedure known as tomographic reconstruction. Initially developed between the 1960s and 1970s, the Computed Tomographic (CT) scanner made exceptional contribution to medicine, which was the first application of the process. In recent years, tomography has spread to different applications. Some examples are Electrical Tomography (using capacitance, resistance, or impedance), Optical Tomography (using light) and Seismic Tomography (using seismic waves).

A general tomographic system includes one or more sources of the wave or signal used, and one or more detectors tuned to detect variations (for example of intensity) of the same wave or signal. Scanning sources and detectors around the object to image, by a relative movement, or by using more of them, the signal or wave penetrates at least part of the object to be imaged, and thus it is affected in a detectable way (for example, its intensity might decrease). The variations of the signals, along with geometrical information (for example the positions of source and detector), is the data that is fed to the tomographic reconstruction process to obtain an object image (tomogram).

Regardless of the specific wave or signal used, tomographic reconstruction is required to obtain the tomogram from the data gathered. When implemented as computer programs or processes, as is most often the case, tomographic reconstruction processes are expensive in terms of computational resources and memory. In general, the reconstruction process complexity is at least proportional to the size of the input information (sinogram) and to the dimensions of the tomogram. As used herein, sinogram refers to sine-based visual data derived from data collected at detectors. The sinogram may be derived from a geometrical transformation of raw input data. To obtain accurate information on the object, generally it would be desirable to increase both the size of the sinogram and the dimensions of the tomogram, thus increasing the computational and memory loads. Increased computational and memory loads are expensive.

In some applications, the interest does not lie in the whole tomogram. Rather, one might be interested in only specific features, which are currently extracted in a successive feature detection process performed on the tomogram. The cost of this further operation is at least proportional to the dimension of the tomogram. Features of interest may be, for example, particular shapes or intensity profiles on the tomogram. In view of the foregoing, it would be desirable to develop optimized methods for feature detection.

SUMMARY OF THE INVENTION

An apparatus includes a processor and a memory connected to the processor. The memory stores instructions executed by the processor to perform a transformation on a detected signal that has penetrated an object of interest to form a sinogram. The sinogram is a sine-based representation of the detected signal. A feature of interest is identified in the sinogram. A tomogram corresponding to the detected signal is reconstructed. The instructions to reconstruct utilize the feature of interest to determine at least one attribute of the tomogram.

BRIEF DESCRIPTION OF THE FIGURES

The invention is more fully appreciated in connection with the following detailed description taken in conjunction with the accompanying drawings, in which.

Like reference numerals refer to corresponding parts throughout the several views of the drawings.

DETAILED DESCRIPTION OF THE INVENTION

Figure 1A:
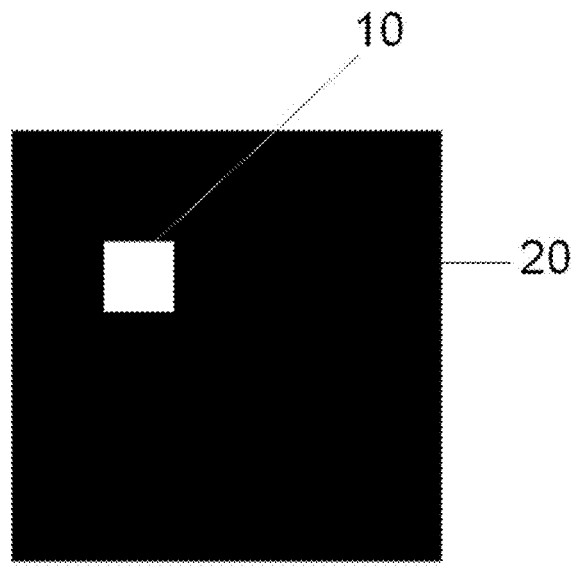
FIG. 1A illustrates a tomogram with a feature of interest.
Figure 1B:
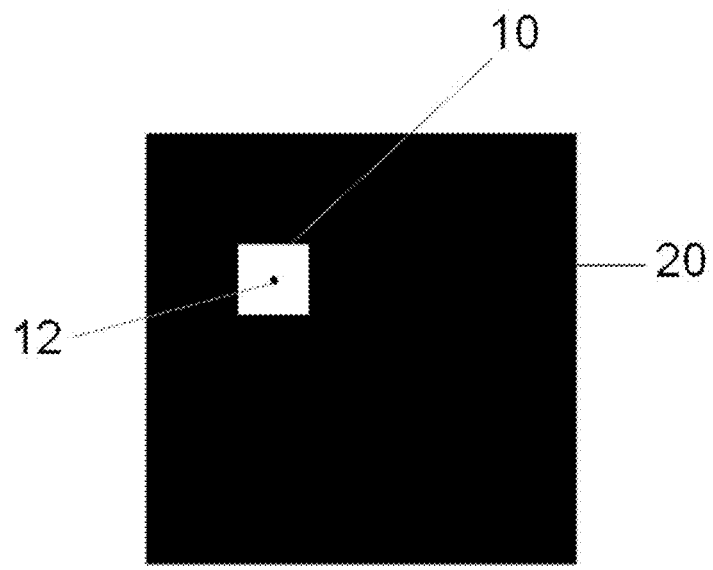
FIG. 1B illustrates a tomogram with a barycenter in a feature of interest.
Figure 1C:
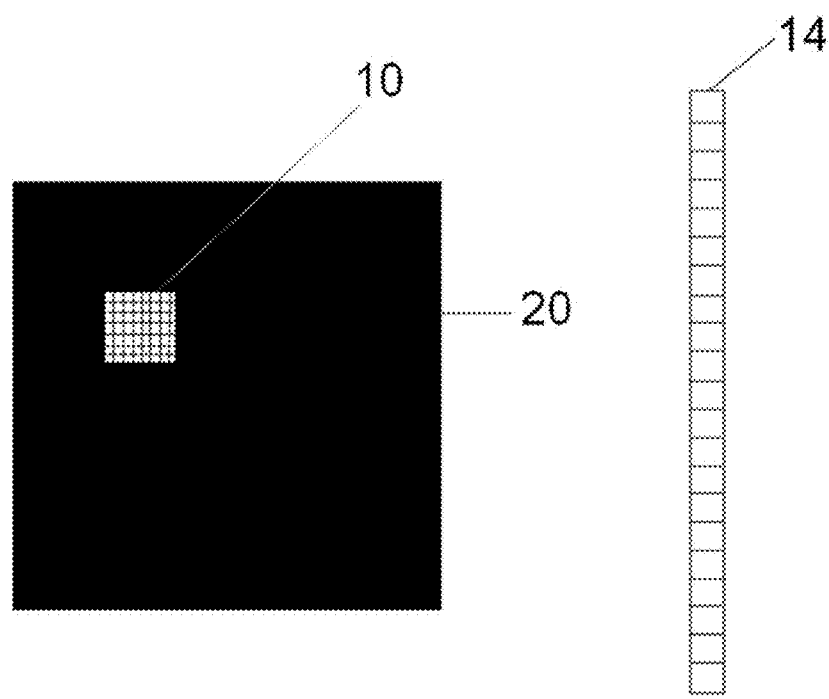
FIG. 1C illustrates a tomogram with an array of points in a feature of interest.
Figure 1D:
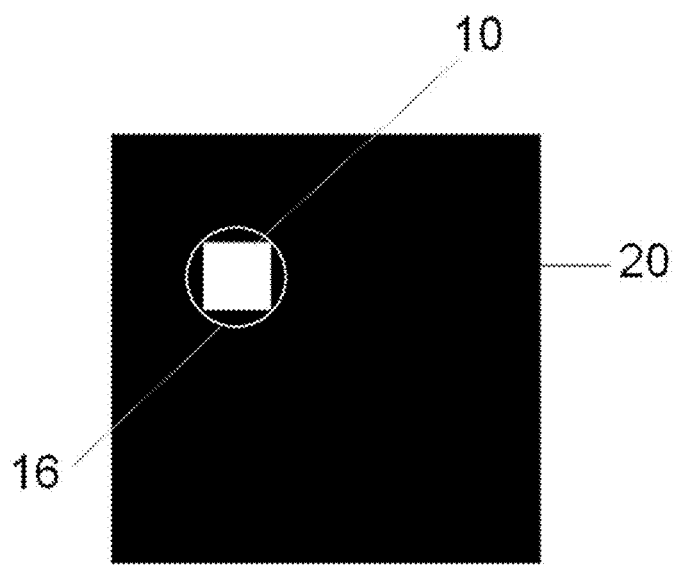
FIG. 1D illustrates a tomogram with an envelope around a feature of interest.

FIG. 1A shows an example of rectangular feature of interest 10 on the tomogram 20. Features of interest may be reported in different ways. For example, in FIG. 1B we represent the coordinates of the barycentre 12 of the feature of interest 10 of FIG. 1A. In FIG. 1C we show an array 14 of all the points in the feature of interest 10 of FIG. 1A. In FIG. 1D we show an envelope 16 of known shape drawn around the feature of interest 10 in FIG. 1A.

The sinogram dimensions are usually smaller than the dimensions of the tomogram. In many practical cases, the tomogram is an image, often in high definition, so it may contain millions of data points. The number of sources and the number of detectors used (or the numbers of their relative positions) give the dimensions of the sinogram; this may result in a few thousands to tens of thousands points.

In this invention, we propose performing a feature detection step on the sinogram to identify the data related to the features of interest of the tomogram. This way, the feature detection step is performed on the smaller data set, with an immediate decrease in computational cost.

The results of this feature detection step can then be used to create the tomogram or a partial area of the tomogram, reconstructing the image only in specific portions of it eventually using only a subset of the sinogram. Hence, the computational cost of the reconstruction step is reduced as well. In some cases, the results of the feature detection performed on the sinogram may be processed to extract only the information of interest, without performing the reconstruction.

Figure 2A:
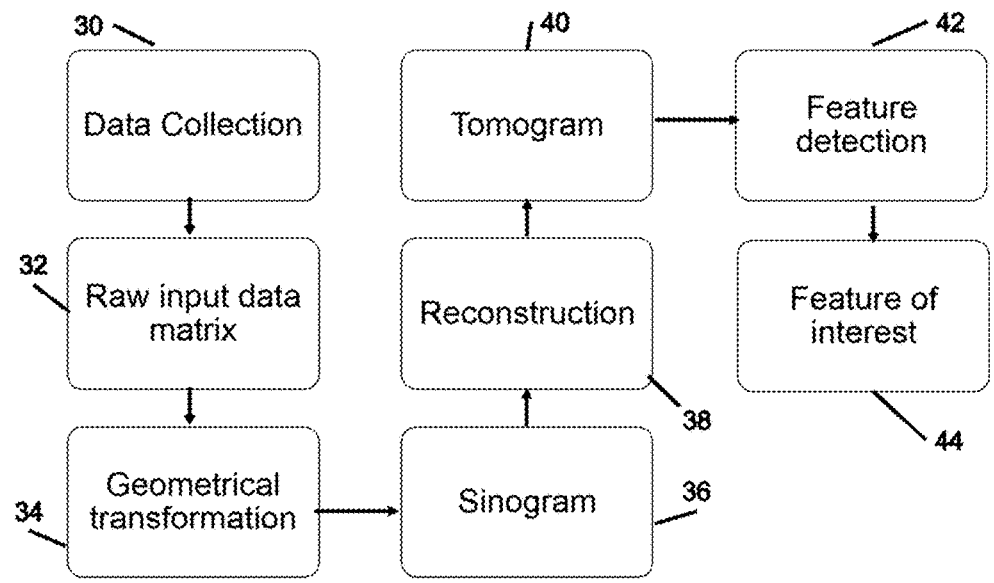
FIG. 2A illustrates processing performed in accordance with an embodiment of the invention.
Figure 2B:
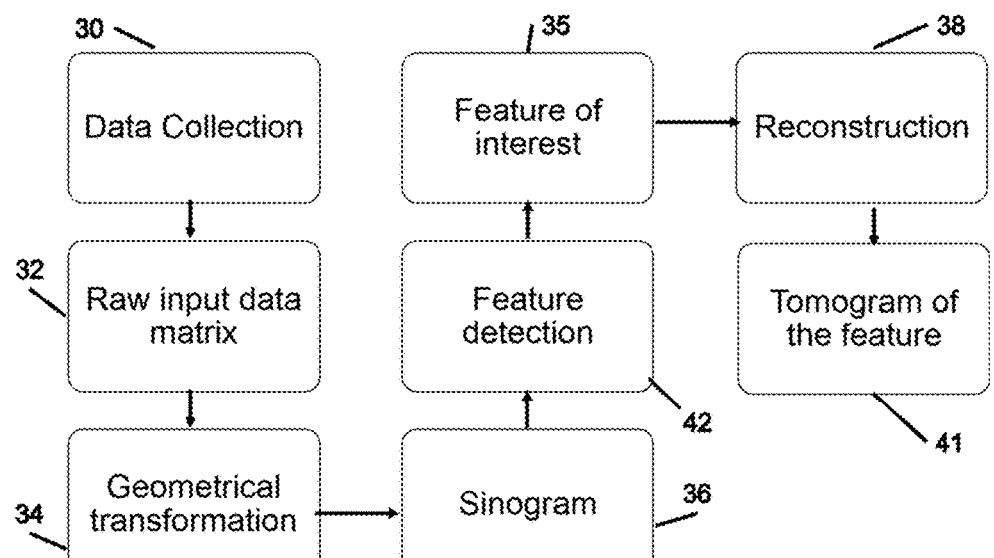
FIG. 2B illustrates processing performed in accordance with another embodiment of the invention.
Figure 2C:
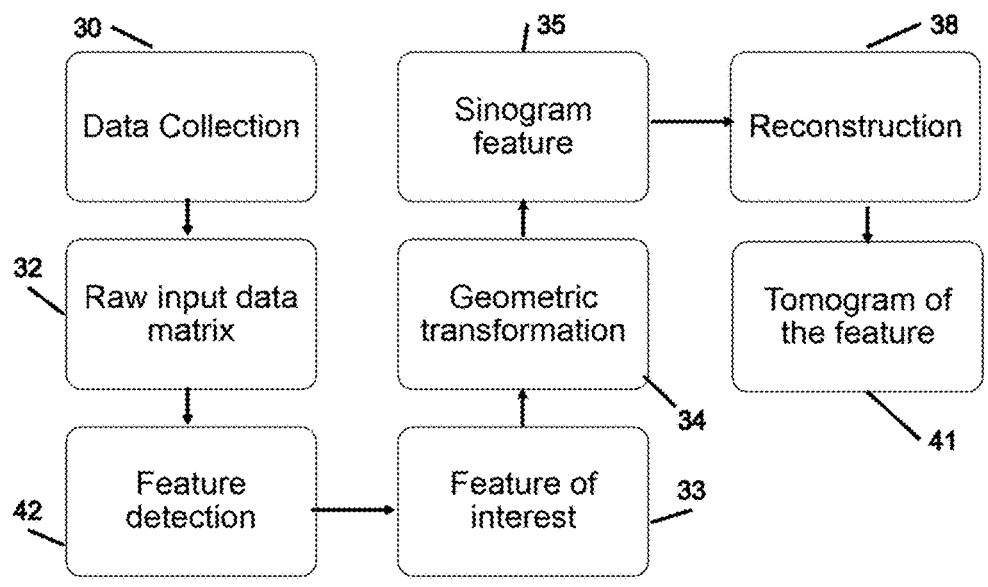
FIG. 2C illustrates processing performed in accordance with still another embodiment of the invention.

FIG. 2A, FIG. 2B and FIG. 2C show flowcharts of some examples of elaboration and reconstruction processes. These processes all start with a data collection step 30, collecting values from the detectors and, usually, storing this data into arrays. Each array defines a profile of the values measured by the detectors and is associated with a boundary distribution of the detectors at every single source. When more sources are used, or a same source in more positions, the arrays are piled to create a raw input data matrix 32.

From this raw input data matrix 32, we show three processes that can be used to obtain information on the features of interest. In the first pathway, shown in FIG. 2A, a transformation 34 is applied on the raw input data 32 to obtain a sinogram 36. This transformation accounts for the specific geometry of the sources and detectors. A reconstruction algorithm 38 is applied to the sinogram 36 to obtain a tomogram 40. Application of a feature detection step 42 allows extracting the feature of interest 44 on the tomogram.

In the second pathway, shown in FIG. 2B, a transformation 34 is applied on the raw input data 32 to obtain a sinogram 36. This transformation accounts for the specific geometry of the sources and detectors. A feature detection step 42 performed on the sinogram 36 extracts the feature of interest 35 on the sinogram. A reconstruction step 38 is then performed using the feature 35 to obtain a partial tomogram of the feature of interest 41. Compared to the first process path from FIG. 2A, in this case the size of the input data for both the feature detection step and the reconstruction step is much smaller.

Feature detection can be performed also directly on the raw input data, having no information of the geometry of the sources and the detectors. This is shown in FIG. 2C. A feature detection step 42 is performed on the raw input data 32, extracting a feature of interest 33. A transformation 34 that accounts for the specific geometry of the sources and detectors is then applied on the feature 33 to obtain a sinogram feature 35. A reconstruction step 38 is then performed using the feature 35 to obtain a partial tomogram of the feature of interest 41.

There are cases in which the information required to characterize a feature might be obtained from sinogram data without performing the reconstruction step. For example, if one obtained the feature of interest 35 on the sinogram, one could extract the coordinates of the barycentre 12 of the feature (see FIG. 1A) directly without reconstruction, with a reduction of computational cost.

In general, the feature detection methods applied to the sinogram are conceptually the same as those available in the scientific literature and applied, for example, in image analysis. There are a number of ways to achieve a feature detection step on a sinogram and they can be divided into two main classes: (1) feature detection methods that operate on all the data of the sinogram and (2) feature detection methods that operate on a partial set of the sinogram.

Figure 3A:
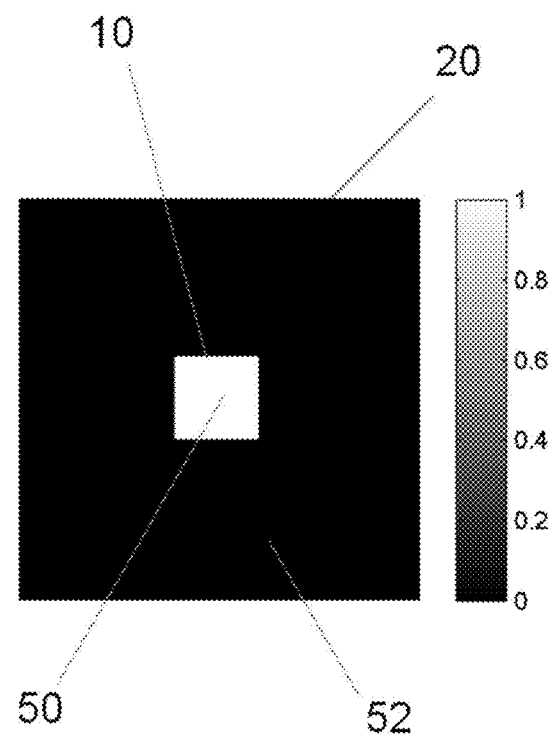
FIG. 3A illustrates a tomogram with a feature of interest having separate areas of interest.
Figure 3B:
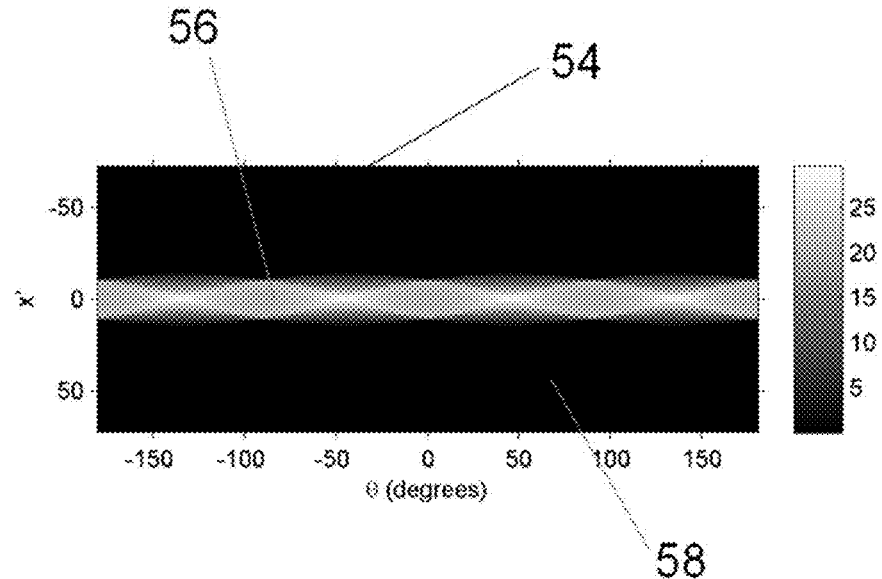
FIG. 3B illustrates a sinogram corresponding to the tomogram of FIG. 3A.

As shown in FIG. 3A, this classification of feature detection methods derives from the possibility to topologically separate an area 50 of the tomogram 20 from another area 52, and at the same time see a distinction on the sinogram 54 (FIG. 3B) between an area 56 (corresponding to the area 50 from the tomogram 20 in FIG. 3A) and an area 58 (corresponding to the area 52 on the tomogram 20 in FIG. 3A), such that an unequivocal correspondence is maintained Any number of feature detection methods may be used in accordance with embodiments of the invention. For example, feature detection methods that operate as filters, using kernel functions as a basic function to be convoluted with the sinogram data, along the rows or columns or both may be used. As a filtering procedure an ad-hoc transform operator can be identified that takes account of both the geometrical information of the distribution of the sources and detectors and the shape of the feature to be detected. This transform operator is applied on the sinogram to obtain a transformed sinogram on which another feature detection method can be applied like, thresholding, masking, blob detection and so on Feature detection methods that process the data of the sinogram that belong to a certain interval or are above/below a certain threshold may be used. Suppose that the data is represented as numbers, this approach entails determining which data points are larger (or smaller) than a pre-set value or data points in a given range. This method has a computational cost that is proportional to the number of comparisons considered. In the cases of interest, this would mean comparing the pre-set number to all values in either the tomogram or the sinogram. As was mentioned above, there is usually a difference of at least two orders of magnitude in the computational cost between the two cases Classical edge detection, point detection and blob detection methods may also be used. Feature detection methods that operate on partial set of data of the sinogram may also be used. These consist of algorithms that explore only a predetermined segment/area (not necessarily consecutive) of the sinogram. For example, the algorithms may be based on lookup tables where for each expected feature of interest on the tomogram there is an associated pattern on the sinogram that can be pre-calculated. The recognition works as a lookup table, comparing the sinogram with the pre-set patterns. Different features in the tomogram correspond to different patterns in the sinogram.

Exclusive-OR (XOR) feature detection algorithms may also be used. Instead of operating on every single value of the sinogram, the feature detection is performed in successive steps. In each step a XOR operation compares the sinogram with predetermined patterns. In general, algorithms that work on all of the data of the sinogram can also be applied to analyze a subset of the sinogram data.

Figure 4A:
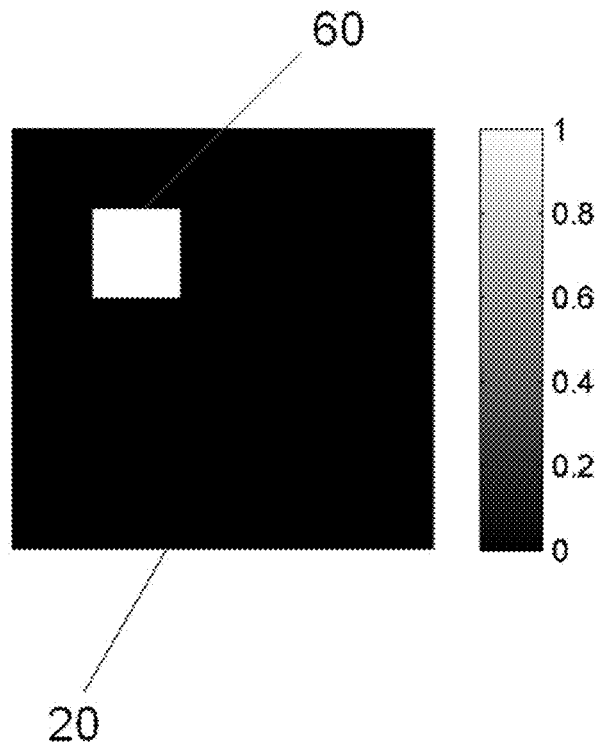
FIG. 4A illustrates a tassel on a tomogram.
Figure 4B:
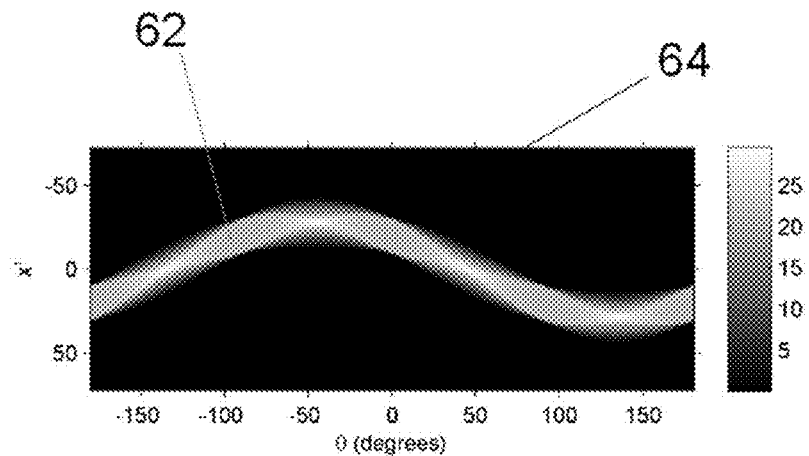
FIG. 4B illustrates the tassel of FIG. 4A in a sinogram.
Figure 4C:
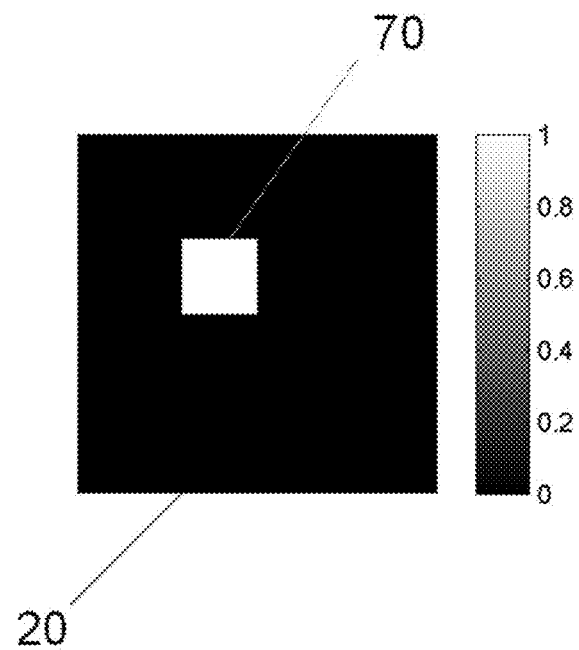
FIG. 4C illustrates another tassel on a tomogram.
Figure 4D:
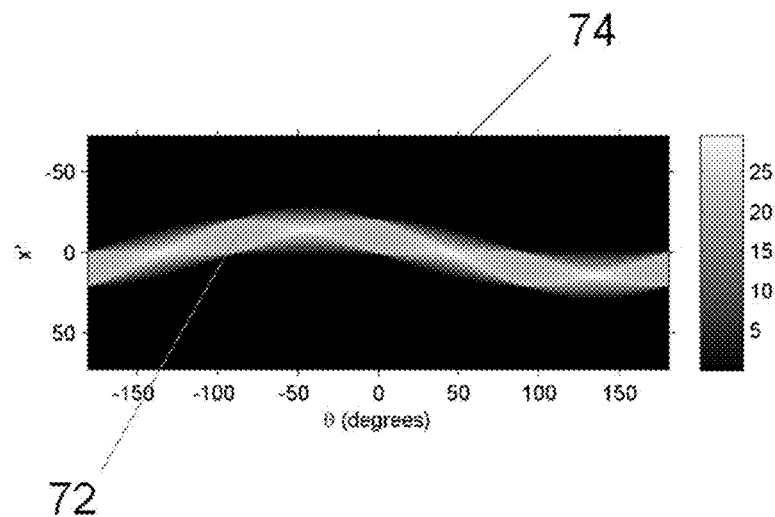
FIG. 4D illustrates the tassel of FIG. 4C in a sinogram.

Other methods of feature detection focus on the possibility to extract the local information of the tomogram through an a priori projection of the known feature from the tomogram to the traditional sinogram. Some examples include tomogram tessellation where the tomogram is tessellated in areas, i.e. regular or Voronoi, which are projected on the sinogram. It is then possible to know if a variation in intensity observed on the sinogram was involved in the corresponding areas. FIG. 4A shows a tassel 60 on the tomogram 20, while FIG. 4B shows the corresponding portion 62 of the sinogram 64. Similarly, FIG. 4C shows a different tassel 70 on the tomogram 20, while FIG. 4D shows the corresponding portion 72 of the sinogram 74.

Figure 5A:
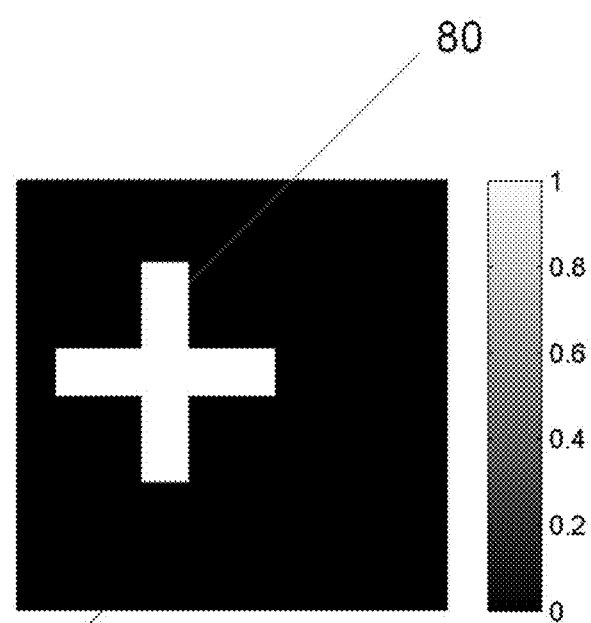
FIG. 5A illustrates a feature of interest in a tomogram.
Figure 5B:
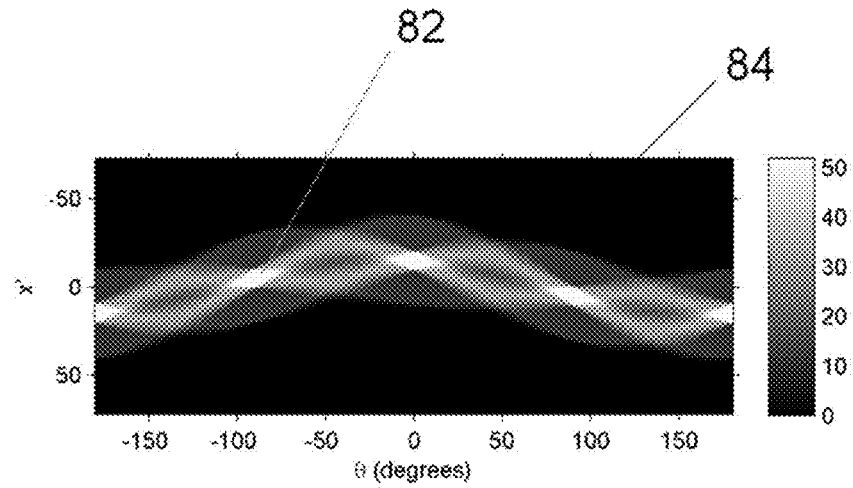
FIG. 5B illustrates the feature of FIG. 5A in a sinogram.

A preloaded feature may also be used by starting from expected features. Their projections on the sinogram are pre-calculated and can be used to search real sinogram data and extract feature information without requiring a formal reconstruction step. FIG. 5A shows an example of feature of interest 80 on a tomogram 20, and FIG. 5B shows its pre-calculated projected feature 82 on a sinogram 84.

Figure 6A:
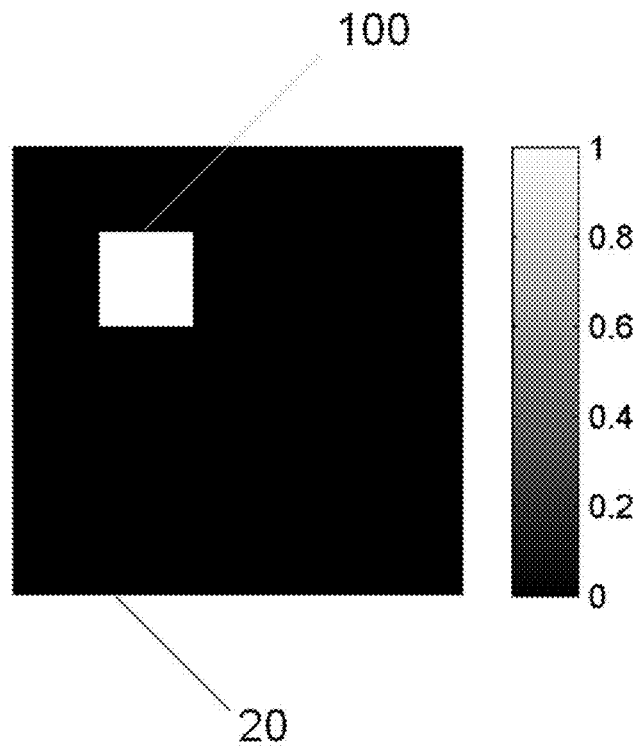
FIG. 6A illustrates a feature of interest.
Figure 6B:
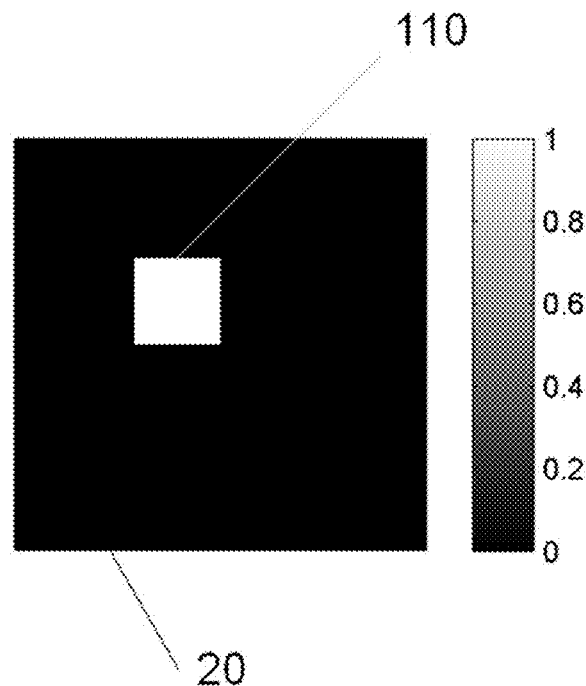
FIG. 6B illustrates a shifted feature of interest.
Figure 6C:
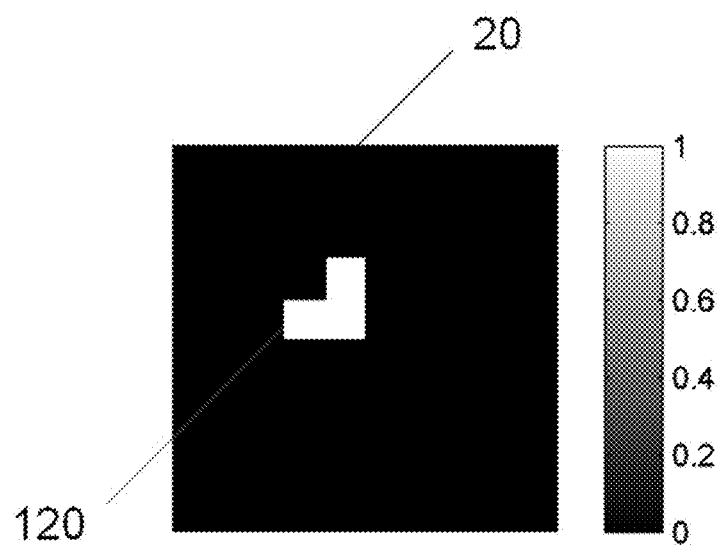
FIG. 6C illustrates the difference in position between FIG. 6A and FIG. 6B.
Figure 6D:
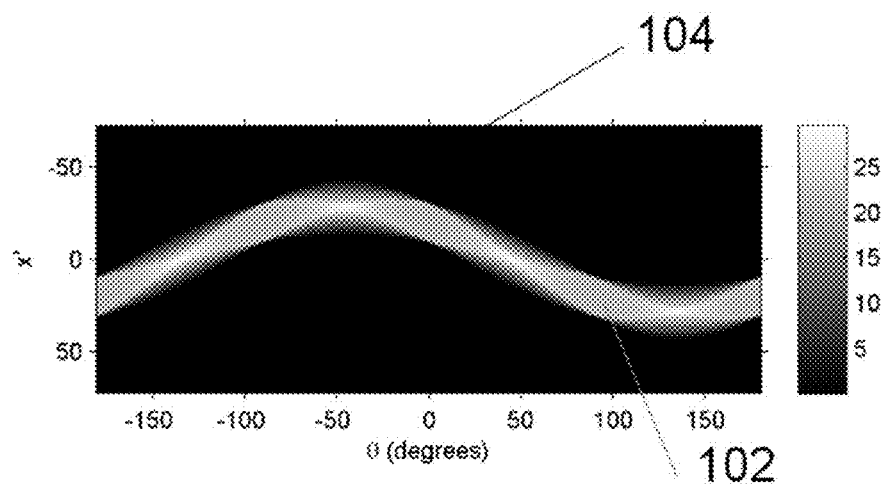
FIG. 6D illustrates a sinogram corresponding to the feature of FIG. 6A.
Figure 6E:
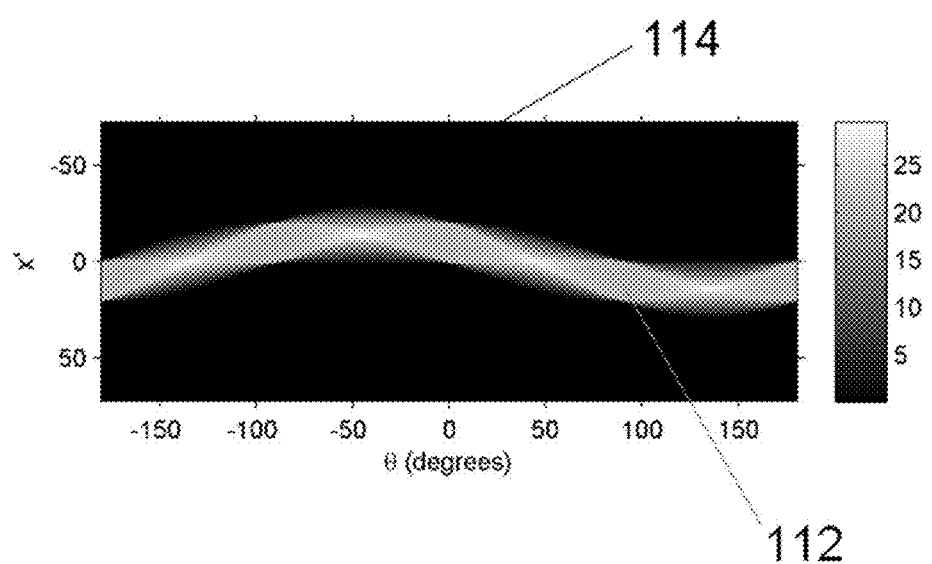
FIG. 6E illustrates a sinogram corresponding to the feature of FIG. 6B.
Figure 6F:
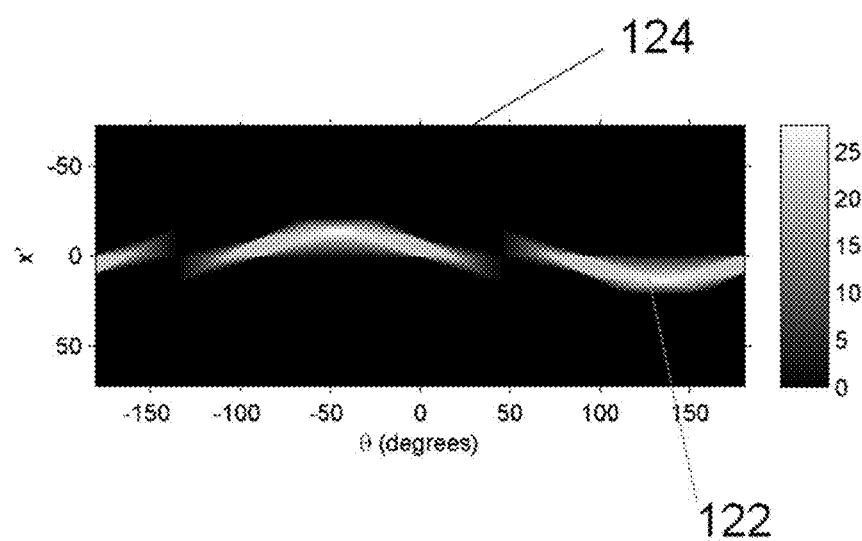
FIG. 6F illustrates feature shift in a sinogram.

The feature detection methods described before can be considered static feature detection methods since they operate on a single sinogram. When the need is to detect a feature that is evolving in time on the tomogram (perhaps moving), then more successive sinograms should be considered in the processing. This results in dynamic feature detection methods. These feature detection methods can be described by considering a variation in the information of the sinogram between two or more sinograms obtained at successive instants in time. As an example of implementation consider a shift in space of the feature of interest 100 on the tomogram 20 of FIG. 6A to the feature of interest 110 on the tomogram 20 of FIG. 6B. The positive difference in position is the area 120 in FIG. 6C. Then the position shift can be identified from the positive difference of the feature 102 on sinogram 104 in FIG. 6D (corresponding to the feature 100 from FIG. 6A) and the feature 112 on sinogram 114 in FIG. 6E (corresponding to the feature 110 in FIG. 6B) resulting in the feature 112 on the sinogram 124 of FIG. 6F.

Regions of interest may be defined by maximum variations. That is, the latest acquired sinogram is subtracted from a previous one and a differential pattern is detected as the maximum variation in the values of the resulting differentiated sinogram. The region of maximum variation on the differentiated sinogram is associated with the dynamic evolution of the feature on the tomogram.

Swipe detection techniques may also be used. That is, after the application of the technique of maximum variation as described before, the detected feature can be processed to obtain some dynamic descriptor, like the main velocity and movement direction and the expansion/contraction rate of the feature (technically the eigenvalues). Those can be used to predict in which areas of sinograms from successive instants in time there will be a higher likelihood to find the features.

As an alternative to the traditional sinogram representation as a matrix of sources and detectors on which to operate the previously described feature detection algorithms, the sinogram can be stored and used for feature detection in a more general data format.

One data format is tree listing. A tree can be constructed from a common root, representing a detector, a source or a couple source/detector can be another node. The choice of which nodes to append where can be guided by some topological rule, like neighborhood of the detectors or sources, or according to some pattern useful for the feature detection process Another data format is feature-defined listing. In this case, data of the sinogram are stored and processed according to a specific representation of data clusters that is suited to identify a single feature or a family of features. As an example of feature-defined listing consider a listing through different analytical functions and their parameters. The different class of analytical functions, like polynomials, sinusoids, polylines and so on, are used to decompose the sinogram. The list contains the values of the parameters associated with the analytical function used to decompose the sinogram. A feature of interest on the sinogram corresponds to a particular occurrence of the listed parameters. For example, suppose that any sinogram feature may be represented as a composition of sinusoids, each defined by a set of parameters. Each level of the feature-defined listing would represent a number of sinusoids; by exploring the feature-defined listing it would be possible to obtain a series of sinusoids that taken together represent a feature.

The alternative representations of the sinogram can become useful in practical implementations because they may allow a faster exploration of the data space they represent, improving on the computational cost of some algorithms. A further advantage of these kinds of representations is that they may allow a simple way to obtain features at different levels of detail or quality by exploring deeper or shallower levels of the representations.

After the feature detection step, the features extracted from the sinogram can go through a post-processing step to gather detailed information. An example is oversampling of the regions of interest by increasing the sampling grid in the sinogram only around the detected feature through interpolation techniques like polynomial or spline fitting. Another possibility is to initially acquire and process only a portion of the data to form the sinogram. After having identified a region of interest, a new acquisition of data is performed that includes more information related to the region of interest. Thus, a higher definition of the feature can be achieved which may be useful for segmentations of one or more features detected as well as to separate two narrow features.

The partial reconstruction mechanism could include a recursive feature detection process. Each feature detected on the sinogram through running a first detection process is fed back to the feature detection process again until criteria on single or multiple optimization parameters are met. The optimization parameter could comprise the amount of entropy of a feature or another image statistical descriptor that specifies the quality of the detected feature. The parameters can be estimated at each recursive step. The stop criteria may consist for example in looking for the maximum or a minimum of a parameter, or for a given differential variation of the parameters between successive recursion steps. In practical cases, the process in the feedback loop could include any previously described feature detection method that operates on all or partial sets of the sinogram. For example, assume one implements a feature detection method using a kernel function, parameters associated with the topology of the kernel function can be considered variables of the recursive process. By defining a priori an optimization parameter, running the loop until the feature detection quality criteria is met will define a convergence of the kernel function topology to the shape of the feature so that it completely suits the feature to be extracted. Alternatively, the feature detection method used recursively may scale with each iteration to highlight finer details. Furthermore, it may be practical to use different feature detection methods in successive recursions, the choice of which may be determined by the quality parameters. This may be particularly advantageous when one has the possibility to use methods optimized for different conditions. For example, a first method may be particularly suited for coarse detection on a large data-set, while a second method may be optimized for detecting fine details in the neighbourhood of given points.

One of the advantages of using optimized processes for feature detection is that some of the computational resources "freed" may be used to improve the quality of the output. For example, spatial features may be described using higher resolution than would be practical by reconstructing the whole tomogram.

In many applications of tomography the computation requirements of the steps involved, in terms of memory and clock cycles, tend to not be critical, as often the results do not need to be produced in real-time. Moreover, the most common practical implementations use rather large equipment, so there is no particular hurdle in building the system with large amounts of memory and computational power. Furthermore, many tomographic systems need to output the whole tomogram, rather than information on specific features. However there are applications where memory may be limited, computational power may be limited, the results of the processing are needed in real time, or almost in real time, or the results needed are specific features rather than the whole tomogram. For example, in a medical imaging system, there may be the need to track an object or probe. This requires real-time detection of its specific signature, regardless of what would be present in the rest of the tomogram. Further examples maybe found in some optical detection systems, for example some touch sensitive layers of a touch display. These systems generally need to report the positions of contacts, or some other contact characteristics, and the output needs to be available in real time, or at least with the minimum possible delay. On top of that, devices including touch sensitive layers may be limited in terms of the available computational resources available.

These later examples are cases where optimizations can be important because they may allow faster detection and tracking of features of interest when compared to the processing of the whole tomogram. This means a higher resolution in time, and can allow a higher spatial resolution for the features.

In sum, one aspect of this disclosure is the use of the sinogram in feature detection rather than the tomogram. Another aspect of the disclosure is the reconstruction of only part of the tomogram based on results from feature detection on the sinogram. Another noteworthy aspect is the extraction of the relevant information directly on the output of the feature detection on the sinogram without any reconstruction process. The use of feature detection methods operative on the whole sinogram and the use of feature detection methods operative on a subset of the sinogram are noteworthy. Pre-determined (pre-computed) sinogram feature templates may be compared with a sinogram to identify features. Dynamic features may be detected on sinogram data by using sinograms from different instants in time. Finally, recursive methods may be used to improve some quality parameters of detected features.

Figure 7:
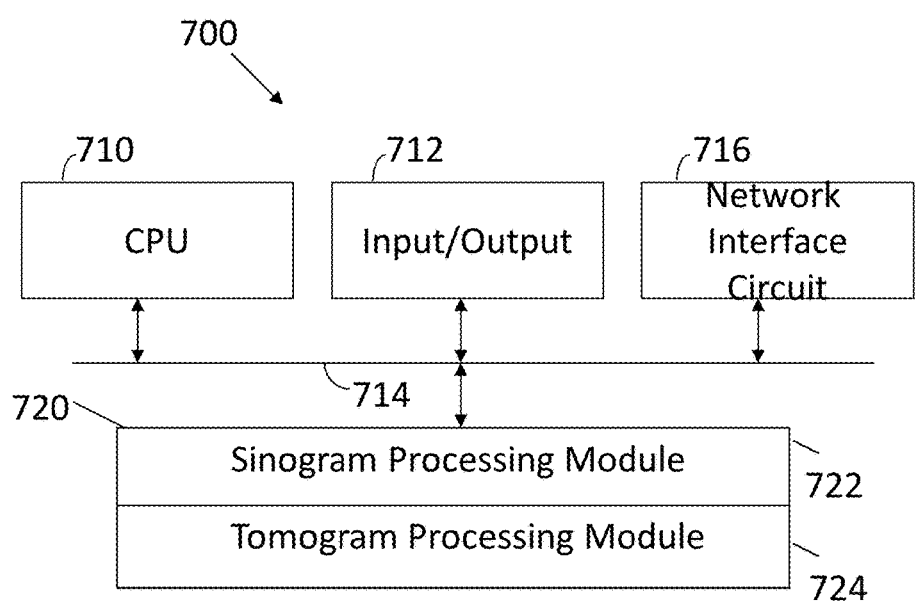
FIG. 7 illustrates a machine configured in accordance with an embodiment of the invention.

FIG. 7 illustrates a machine 700 configured in accordance with an embodiment of the invention. The machine 700 includes standard components, such as a central processing unit or processor 710 connected to input/output devices 712 via a bus 714. The input/output devices may include ports for receiving signals from detectors collecting signals that have penetrated an object of interest. The input/output devices 712 may also include a keyboard, mouse, touch display and the like. A network interface circuit 716 is also connected to the bus 714 to provide connectivity to a network (not shown). A memory 720 is also connected to the bus 714. The memory 720 stores instructions executed by the processor 710 to implement operations of the invention. In one embodiment, the instructions include a sinogram processing module 722. By way of example, the sinogram processing module 722 may implement operations 30-36 of FIG. 2A or operations 30-42 of FIG. 2B. The memory 720 also stores a tomogram processing module 724. By way of example, the tomogram processing module 722 may implement operations 38-44 of FIG. 2A or operations 38-41 of FIG. 2B.

An embodiment of the present invention relates to a computer storage product with a non-transitory computer readable storage medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media, optical media, magneto-optical media and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using JAVA®, C++, or other object-oriented programming language and development tools. Another embodiment of the invention may be implemented in hardwired circuitry in place of, or in combination with, machine-executable software instructions.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. An apparatus, comprising:
a processor; and
a memory connected to the processor, the memory storing instructions executed by the processor to:
perform a transformation on a detected signal that has penetrated an object of interest to form a sinogram, wherein the sinogram is a sine-based representation of the detected signal,
identify a feature of interest in the sinogram, and
reconstruct a tomogram corresponding to the detected signal, wherein the instructions to reconstruct utilize the feature of interest to determine at least one attribute of the tomogram, wherein the at least one attribute of the tomogram is limited to the feature of interest.

2. The apparatus of claim 1 wherein the instructions to identify include instructions to perform recursive processing.

3. The apparatus of claim 1 wherein the instructions to identify include instructions to identify dynamic features from sinograms from different instances in time.

4. An apparatus, comprising:
a processor; and
a memory connected to the processor, the memory storing instructions executed by the processor to:
perform a transformation on a detected signal that has penetrated an object of interest to form a sinogram, wherein the sinogram is a sine-based representation of the detected signal,
identify a feature of interest in the sinogram, and
reconstruct a tomogram corresponding to the detected signal, wherein the instructions to reconstruct utilize the feature of interest to determine at least one attribute of the tomogram, wherein the at least one attribute of the tomogram is a tomogram with a first resolution for the feature of interest and a second resolution for all remaining content, wherein the first resolution is higher than the second resolution.

5. The apparatus of claim 4 wherein the instructions to identify include instructions to perform recursive processing.

6. The apparatus of claim 4 wherein the instructions to identify include instructions to identify dynamic features from sinograms from different instances in time.

7. An apparatus, comprising:
a processor; and
a memory connected to the processor, the memory storing instructions executed by the processor to:
perform a transformation on a detected signal that has penetrated an object of interest to form a sinogram, wherein the sinogram is a sine-based representation of the detected signal,
identify a feature of interest in the sinogram, and
reconstruct a tomogram corresponding to the detected signal, wherein the instructions to reconstruct utilize the feature of interest to determine at least one attribute of the tomogram, wherein the instructions to identify include instructions to identify from pre-computed sinogram features.

8. The apparatus of claim 7 wherein the instructions to identify include instructions to perform recursive processing.

9. The apparatus of claim 7 wherein the instructions to identify include instructions to identify dynamic features from sinograms from different instances in time.

* * * * *